(12) United States Patent
Molnar et al.

(10) Patent No.: US 10,114,760 B2
(45) Date of Patent: Oct. 30, 2018

(54) METHOD AND SYSTEM FOR IMPLEMENTING MULTI-STAGE TRANSLATION OF VIRTUAL ADDRESSES

(71) Applicant: NVIDIA Corporation, Santa Clara, CA (US)

(72) Inventors: Steven E. Molnar, Chapel Hill, NC (US); Jay Kishora Gupta, Bangalore (IN); James Leroy Deming, Madison, AL (US); Samuel Hammond Duncan, Arlington, MA (US); Jeffrey Smith, Santa Clara, CA (US)

(73) Assignee: NVIDIA CORPORATION, Santa Clara, CA (US)

( * ) Notice: Subject to any disclaimer, the term of this patent is extended or adjusted under 35 U.S.C. 154(b) by 697 days.

(21) Appl. No.: 14/155,278

(22) Filed: Jan. 14, 2014

(65) Prior Publication Data
US 2015/0199280 A1 Jul. 16, 2015

(51) Int. Cl.
*G06F 12/1027* (2016.01)
*G06F 12/1009* (2016.01)

(52) U.S. Cl.
CPC ...... *G06F 12/1027* (2013.01); *G06F 12/1009* (2013.01); *G06F 2212/1016* (2013.01); *G06F 2212/651* (2013.01); *G06F 2212/682* (2013.01)

(58) Field of Classification Search
CPC ............. G06F 12/1009; G06F 12/1027; G06F 2212/1016; G06F 2212/651; G06F 2212/682
See application file for complete search history.

(56) References Cited

U.S. PATENT DOCUMENTS

| | | | | |
|---|---|---|---|---|
| 5,530,820 | A * | 6/1996 | Onodera | G06F 12/109 711/203 |
| 5,752,275 | A * | 5/1998 | Hammond | G06F 12/1027 711/128 |
| 7,171,539 | B2 * | 1/2007 | Mansell | G06F 12/1491 711/203 |
| 7,545,382 | B1 | 6/2009 | Montrym et al. | |
| 2009/0158003 | A1 * | 6/2009 | Sathaye | G06F 12/10 711/206 |
| 2009/0222816 | A1 * | 9/2009 | Mansell | G06F 12/145 718/1 |
| 2009/0244074 | A1 * | 10/2009 | Montrym | G06T 1/60 345/522 |
| 2009/0320048 | A1 * | 12/2009 | Watt | G06F 9/4812 719/319 |
| 2011/0023027 | A1 * | 1/2011 | Kegel | G06F 12/10 718/1 |

(Continued)

*Primary Examiner* — Eric T Oberly
(74) *Attorney, Agent, or Firm* — Zilka-Kotab, P.C.

(57) ABSTRACT

A system and method are provided for implementing multi-stage translation of virtual addresses. The method includes the steps of receiving, at a first memory management unit, a memory request including a virtual address in a first address space, translating the virtual address to generate a second virtual address in a second address space, and transmitting a modified memory request including the second virtual address to a second memory management unit. The second memory management unit is configured to translate the second virtual address to generate a physical address in a third address space. The physical address is associated with a location in a memory.

20 Claims, 11 Drawing Sheets

(56) References Cited

U.S. PATENT DOCUMENTS

2013/0262736 A1* 10/2013 Kegel ................. G06F 12/1081
                                                        711/3
2014/0282501 A1*  9/2014 Zeng .................. G06F 9/45545
                                                        718/1

* cited by examiner

METHOD AND SYSTEM FOR IMPLEMENTING MULTI-STAGE TRANSLATION OF VIRTUAL ADDRESSES

FIELD OF THE INVENTION

The present invention relates to virtual addresses, and more particularly to multi-stage translation of virtual addresses to physical addresses.

BACKGROUND

Virtualization is commonly used by memory systems in order to map non-contiguous physical memory addresses to a contiguous address space. An operating system manages the virtual address space, assigning blocks of virtual addresses to blocks of physical addresses. A hardware unit included in the processor, commonly known as a memory management unit (MMU), is configured to translate the virtual addresses into the correct physical addresses using a page table. The page table maps blocks of virtual addresses, called pages, to blocks of physical memory. Each page table entry for a virtual address range may include a base physical address that identifies the first address in a range of physical addresses corresponding to the virtual address range. The page table entry may also include various attributes associated with the page such as write protection bits, access tags, compression information, and so forth.

Various architectures define pages of varying sizes. For example, the ARMv7-x architecture specified for many ARM® Cortex processors, defines pages of 4 KB, 64 KB, 1 MB, and 16 MB using a two-level hierarchical page table. Some architectures (or operating systems) only allow a single page size of, for example, 4 KB. However some attributes associated with pages may apply to larger regions of memory than a single 4 KB page. Thus, storing such attributes inside each page table entry is redundant. Having smaller page sizes creates large page tables for the same address space and may cause more cache misses in the translation lookaside buffers (TLBs) (i.e., smaller page sizes means the same number of page table entries stored in the TLB corresponds to a smaller range of addresses). Fetching large page table entries for these smaller pages is inefficient. Thus, there is a need for addressing these issues and/or other issues associated with the prior art.

SUMMARY

A system and method are provided for implementing multi-stage translation of virtual addresses. The method includes the steps of receiving, at a first memory management unit, a memory request including a virtual address in a first address space, translating the virtual address to generate a second virtual address in a second address space, and transmitting a modified memory request including the second virtual address to a second memory management unit. The second memory management unit is configured to translate the second virtual address to generate a physical address in a third address space. The physical address is associated with a location in a memory.

DETAILED DESCRIPTION

A virtual memory architecture is defined that enables multi-stage translation of a virtual address to a physical address by two or more MMUs. In a first translation, a first MMU translates an application virtual address (AVA) to generate an intermediate virtual address (IVA). The first translation may be based on page tables associated with pages of arbitrary size, limited only by the hardware implementation of the MMU. The intermediate virtual address is then forwarded to a second MMU that translates the IVA to generate a physical address (PA) that represents a location in a memory device such as a dynamic random access memory (DRAM).

The page tables used for the first translation may be associated with pages that are larger than the pages required by the operating system. For example, the first translation of the AVA to the IVA may utilize page tables associated with 64 KB pages while the second translation of the IVA to the PA may utilize page tables associated with 4 KB pages. Attributes that are consistent across the larger pages may be stored in the page table entries associated with the first page table while attributes that vary for adjacent 4 KB pages may be stored in the second page table. Such an implementation enables efficiencies to be realized during operation that may be better than could be implemented using a single stage translation limited to a page size compatible with the operating system. For example, intermediate addressing may enable algorithms that require addresses being contiguous over a larger range than 4 KB to be implemented with operating systems that require 4 KB pages at the lowest level of translation.

Figure 1:
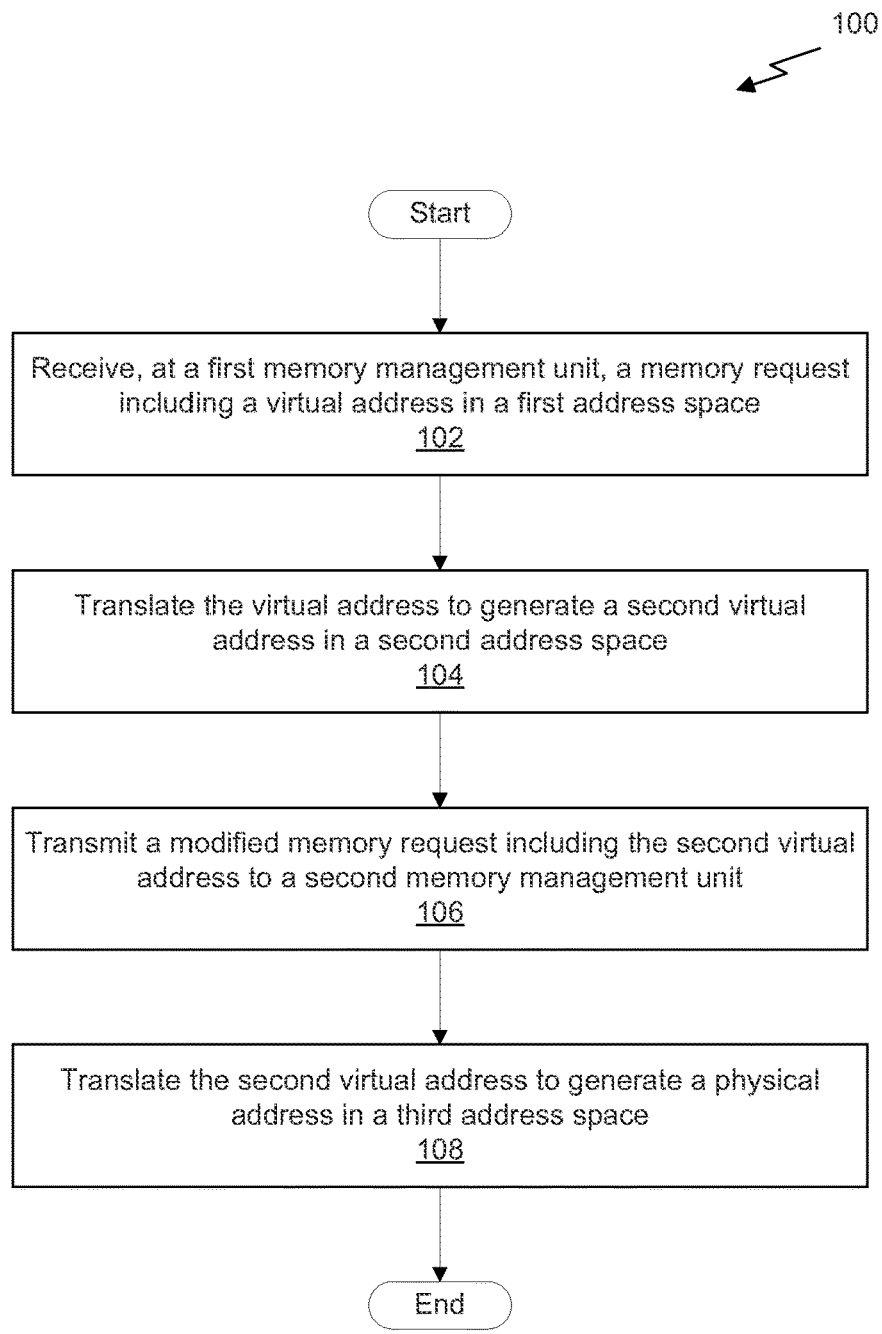
FIG. 1 illustrates a flowchart of a method for multi-stage translation of a virtual address to a physical address, in accordance with one embodiment.

FIG. 1 illustrates a flowchart of a method 100 for multi-stage translation of a virtual address to a physical address, in accordance with one embodiment. At step 102, a first memory management unit receives a memory request including a virtual address in a first address space. In one embodiment, the first address space is an application address space. At step 104, the first memory management unit translates the virtual address to generate a second virtual address in a second address space. At step 106, the first memory management unit transmits a modified memory request including the second virtual address to a second memory management unit. At step 108, the second memory management unit translates the second virtual address to generate a physical address in a third address space. The physical address represents a location in a memory. The memory may be coupled to the second MMU. As used herein, the term coupled may refer to a direct connection or an indirect connection through one or more intermediate units/hardware including, but not limited to, a memory coupled to a memory management unit via a crossbar or other type of interconnection network or a memory coupled to the memory management unit over a network.

More illustrative information will now be set forth regarding various optional architectures and features with which the foregoing framework may or may not be implemented, per the desires of the user. It should be strongly noted that the following information is set forth for illustrative purposes and should not be construed as limiting in any manner. Any of the following features may be optionally incorporated with or without the exclusion of other features described.

Figure 2:
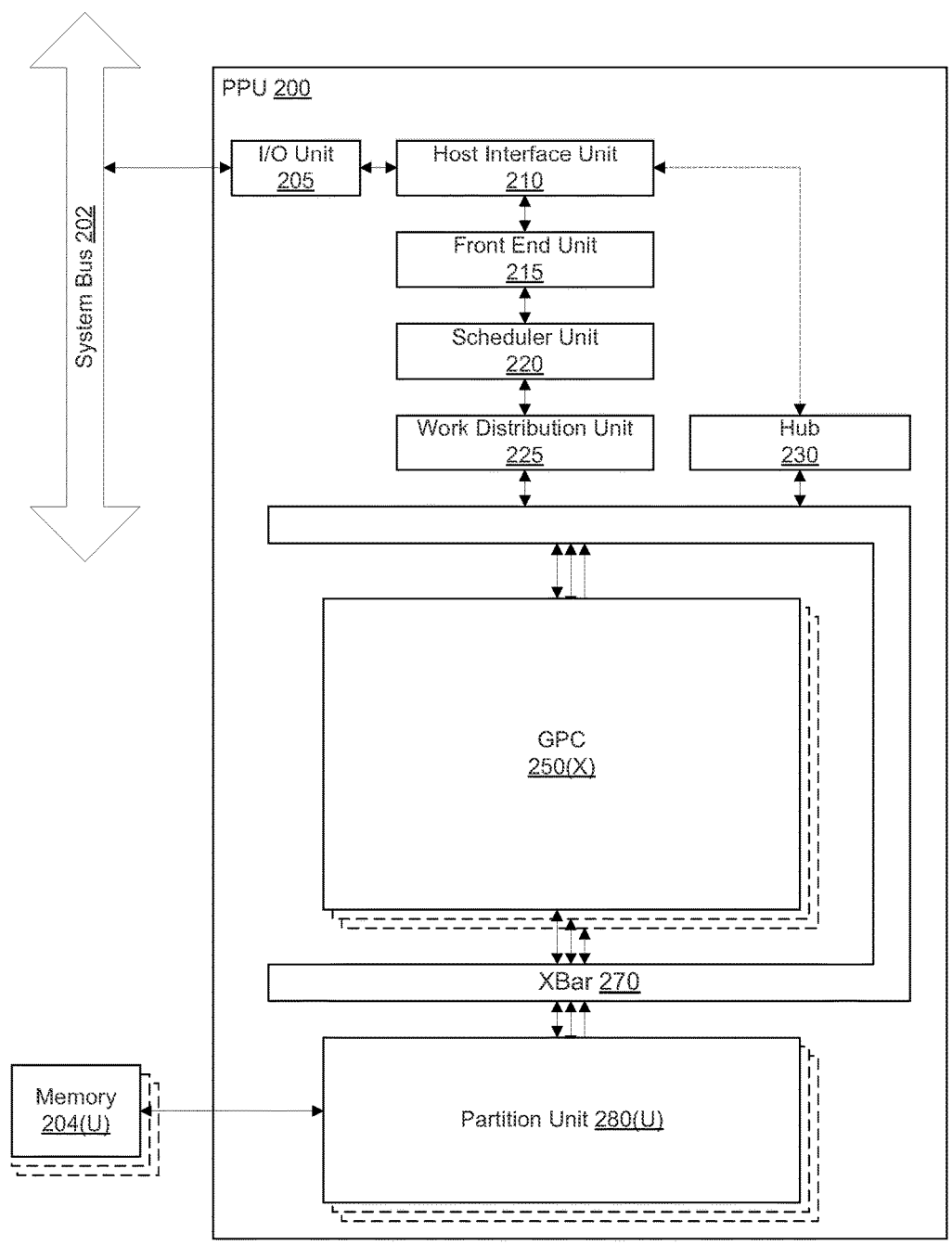
FIG. 2 illustrates a parallel processing unit, if accordance with one embodiment.

FIG. 2 illustrates a parallel processing unit (PPU) 200, in accordance with one embodiment. In one embodiment, the PPU 200 is a multi-threaded processor that is implemented on one or more integrated circuit devices. The PPU 200 is a latency hiding architecture designed to process a large number of threads in parallel. A thread (i.e., a thread of execution) is an instantiation of a set of instructions configured to be executed by the PPU 200. In one embodiment, the PPU 200 is a graphics processing unit (GPU) configured to implement a graphics rendering pipeline for processing three-dimensional (3D) graphics data in order to generate two-dimensional (2D) image data for display on a display device such as a liquid crystal display (LCD) device. In other embodiments, the PPU 200 may be utilized for performing general-purpose computations. While one exemplary parallel processor is provided herein for illustrative purposes, it should be strongly noted that such processor is set forth for illustrative purposes only, and that any processor may be employed to supplement and/or substitute for the same.

As shown in FIG. 2, the PPU 200 includes an Input/Output (I/O) unit 205, a host interface unit 210, a front end unit 215, a scheduler unit 220, a work distribution unit 225, a hub 230, a crossbar (Xbar) 270, one or more general processing clusters (GPCs) 250, and one or more partition units 280. The PPU 200 may be connected to a host processor or other peripheral devices via a system bus 202. The PPU 200 may also be connected to a local memory comprising a number of memory devices 204. In one embodiment, the local memory may comprise a number of dynamic random access memory (DRAM) devices.

The I/O unit 205 is configured to transmit and receive communications (i.e., commands, data, etc.) from a host processor (not shown) over the system bus 202. The I/O unit 205 may communicate with the host processor directly via the system bus 202 or through one or more intermediate devices such as a memory bridge. In one embodiment, the I/O unit 205 Implements a Peripheral Component Interconnect Express (PCIe) interface for communications over a PCIe bus. In alternative embodiments, the I/O unit 205 may implement other types of well-known interfaces for communicating with external devices.

The I/O unit 205 is coupled to a host interface unit 210 that decodes packets received via the system bus 202. In one embodiment, the packets represent commands configured to cause the PPU 200 to perform various operations. The host interface unit 210 transmits the decoded commands to various other units of the PPU 200 as the commands may specify. For example, some commands may be transmitted to the front end unit 215. Other commands may be transmitted to the hub 230 or other units of the PPU 200 such as one or more copy engines, a video encoder, a video decoder, a power management unit, etc. (not explicitly shown). In other words, the host interface unit 210 is configured to route communications between and among the various logical units of the PPU 200.

In one embodiment, a program executed by the host processor encodes a command stream in a buffer that provides workloads to the PPU 200 for processing. A workload may comprise a number of instructions and data to be processed by those instructions. The buffer is a region in a memory that is accessible (i.e., read/write) by both the host processor and the PPU 200. For example, the host interface unit 210 may be configured to access the buffer in a system memory connected to the system bus 202 via memory requests transmitted over the system bus 202 by the I/O unit 205. In one embodiment, the host processor writes the command stream to the buffer and then transmits a pointer to the start of the command stream to the PPU 200. The host interface unit 210 provides the front end unit 215 with pointers to one or more command streams. The front end unit 215 manages the one or more streams, reading commands from the streams and forwarding commands to the various units of the PPU 200.

The front end unit 215 is coupled to a scheduler unit 220 that configures the various GPCs 250 to process tasks defined by the one or more streams. The scheduler unit 220 is configured to track state information related to the various tasks managed by the scheduler unit 220. The state may indicate which GPC 250 a task is assigned to, whether the task is active or inactive, a priority level associated with the task, and so forth. The scheduler unit 220 manages the execution of a plurality of tasks on the one or more GPCs 250.

The scheduler unit 220 is coupled to a work distribution unit 225 that is configured to dispatch tasks for execution on the GPCs 250. The work distribution unit 225 may track a number of scheduled tasks received from the scheduler unit 220. In one embodiment, the work distribution unit 225 manages a pending task pool and an active task pool for each of the GPCs 250. The pending task pool may comprise a number of slots (e.g., 16 slots) that contain tasks assigned to be processed by a particular GPC 250. The active task pool may comprise a number of slots (e.g., 4 slots) for tasks that are actively being processed by the GPCs 250. As a GPC 250 finishes the execution of a task, that task is evicted from the active task pool for the GPC 250 and one of the other tasks from the pending task pool is selected and scheduled for execution on the GPC 250. If an active task has been idle on the GPC 250, such as while waiting for a data dependency to be resolved, then the active task may be evicted from the GPC 250 and returned to the pending task pool while another task in the pending task pool is selected and scheduled for execution on the GPC 250.

The work distribution unit 225 communicates with the one or more GPCs 250 via a XBar 270. The XBar 270 is an interconnect network that couples many of the units of the PPU 200 to other units of the PPU 200. For example, the XBar 270 may be configured to couple the work distribution unit 225 to a particular GPC 250. Although not shown explicitly, one or more other units of the PPU 200 are coupled to the host unit 210. The other units may also be connected to the XBar 270 via a hub 230.

The tasks are managed by the scheduler unit 220 and dispatched to a GPC 250 by the work distribution unit 225. The GPC 250 is configured to process the task and generate results. The results may be consumed by other tasks within the GPC 250, routed to a different GPC 250 via the XBar 270, or stored in the memory 204. The results can be written to the memory 204 via the partition units 280, which implement a memory interface for reading and writing data to/from the memory 204. In one embodiment, the PPU 200 includes a number U of partition units 280 that is equal to the number of separate and distinct memory devices 204 coupled to the PPU 200. A partition unit 280 will be described in more detail below in conjunction with FIG. 3B.

In one embodiment, a host processor executes a driver kernel that implements an application programming interface (API) that enables one or more applications executing on the host processor to schedule operations for execution on the PPU 200. An application may generate instructions (i.e., API calls) that cause the driver kernel to generate one or more tasks for execution by the PPU 200. The driver kernel outputs tasks to one or more streams being processed by the PPU 200. Each task may comprise one or more groups of related threads, referred to herein as a warp. A thread block may refer to a plurality of groups of threads including instructions to perform the task. Threads in the same group of threads may exchange data through shared memory. In one embodiment, a group of threads comprises 32 related threads.

Figure 3A:
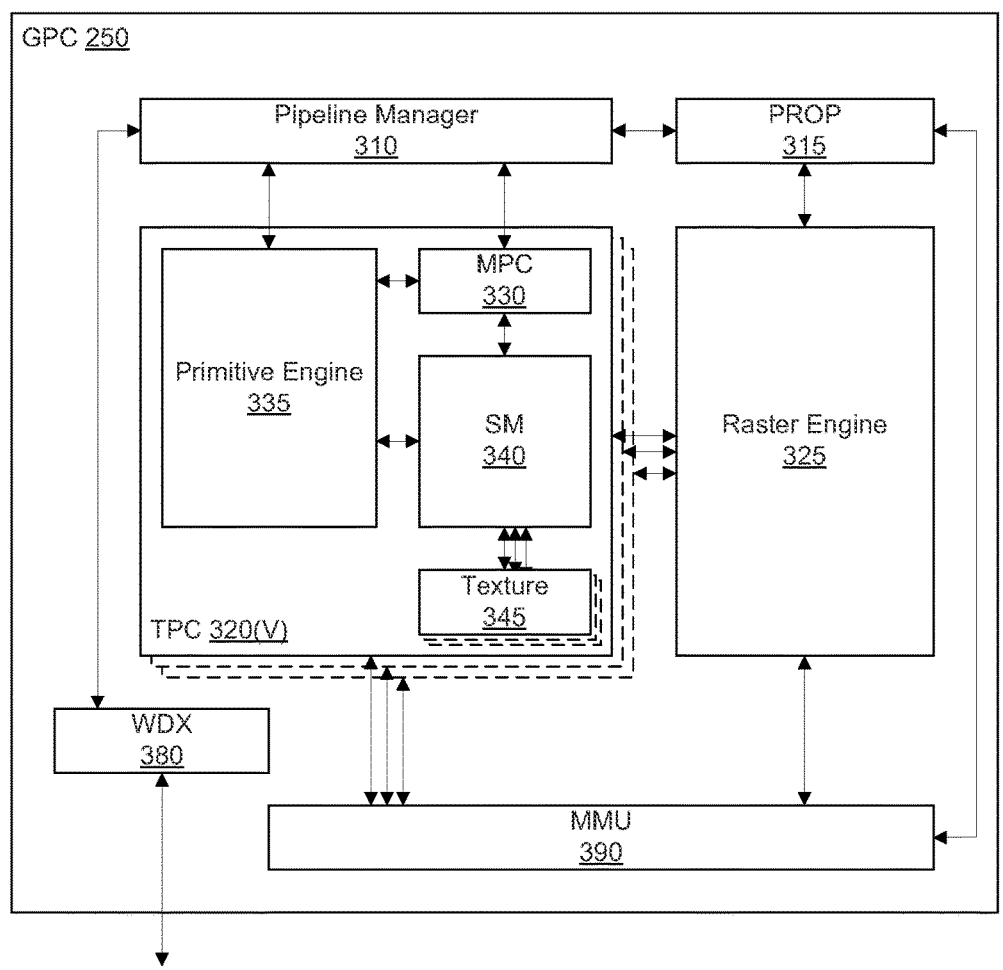
FIG. 3A illustrates a general processing cluster of the parallel processing unit of FIG. 2, in accordance with one embodiment.

FIG. 3A illustrates a GPC 250 of the PPU 200 of FIG. 2, in accordance with one embodiment. As shown in FIG. 3A, each GPC 250 includes a number of hardware units for processing tasks. In one embodiment, each GPC 250 includes a pipeline manager 310, a pre-raster operations unit (PROP) 315, a raster engine 325, a work distribution crossbar (WDX) 380, a memory management unit (MMU) 390, and one or more Texture Processing Clusters (TPCs) 320. It will be appreciated that the GPC 250 of FIG. 3A may include other hardware units in lieu of or in addition to the units shown in FIG. 3A.

In one embodiment, the operation of the GPC 250 is controlled by the pipeline manager 310. The pipeline manager 310 manages the configuration of the one or more TPCs 320 for processing tasks allocated to the GPC 250. In one embodiment, the pipeline manager 310 may configure at least one of the one or more TPCs 320 to implement at least a portion of a graphics rendering pipeline. For example, a TPC 320 may be configured to execute a vertex shader program on the programmable streaming multiprocessor (SM) 340. The pipeline manager 310 may also be configured to route packets received from the work distribution unit 225 to the appropriate logical units within the GPC 250. For example, some packets may be routed to fixed function hardware units in the PROP 315 and/or raster engine 325 while other packets may be routed to the TPCs 320 for processing by the primitive engine 335 or the SM 340.

The PROP unit 315 is configured to route data generated by the raster engine 325 and the TPCs 320 to a Raster Operations (ROP) unit in the partition unit 280, described in more detail below. The PROP unit 315 may also be configured to perform optimizations for color blending, organize pixel data, perform address translations, and the like.

The raster engine 325 includes a number of fixed function hardware units configured to perform various raster operations. In one embodiment, the raster engine 325 includes a setup engine, a course raster engine, a culling engine, a clipping engine, a fine raster engine, and a tile coalescing engine. The setup engine receives transformed vertices and generates plane equations associated with the geometric primitive defined by the vertices. The plane equations are transmitted to the coarse raster engine to generate coverage information (e.g., an x,y coverage mask for a tile) for the primitive. The output of the coarse raster engine may transmitted to the culling engine where fragments associated with the primitive that fail a z-test are culled, and transmitted to a clipping engine where fragments lying outside a viewing frustum are clipped. Those fragments that survive clipping and culling may be passed to a fine raster engine to generate attributes for the pixel fragments based on the plane equations generated by the setup engine. The output of the raster engine 380 comprises fragments to be processed, for example, by a fragment shader implemented within a TPC 320.

Each TPC 320 included in the GPC 250 includes an M-Pipe Controller (MPC) 330, a primitive engine 335, an SM 340, and one or more texture units 345. The MPC 330 controls the operation of the TPC 320, routing packets received from the pipeline manager 310 to the appropriate units in the TPC 320. For example, packets associated with a vertex may be routed to the primitive engine 335, which is configured to fetch vertex attributes associated with the vertex from the memory 204. In contrast, packets associated with a shader program may be transmitted to the SM 340.

In one embodiment, the texture units 345 are configured to load texture maps (e.g., a 2D array of texels) from the memory 204 and sample the texture maps to produce sampled texture values for use in shader programs executed by the SM 340. The texture units 345 implement texture operations such as filtering operations using mip-maps (i.e., texture maps of varying levels of detail). In one embodiment, each TPC 320 includes four (4) texture units 345.

The SM 340 comprises a programmable streaming processor that is configured to process tasks represented by a number of threads. Each SM 340 is multi-threaded and configured to execute a plurality of threads (e.g., 32 threads) from a particular group of threads concurrently. In one embodiment, the SM 340 implements a SIMD (Single-Instruction, Multiple-Data) architecture where each thread in a group of threads (i.e., a warp) is configured to process a different set of data based on the same set of instructions. All threads in the group of threads execute the same instructions. In another embodiment, the SM 340 implements a SIMT (Single-Instruction, Multiple Thread) architecture where each thread in a group of threads is configured to process a different set of data based on the same set of instructions, but where individual threads in the group of threads are allowed to diverge during execution. In other words, when an instruction for the group of threads is dispatched for execution, some threads in the group of threads may be active, thereby executing the instruction, while other threads in the group of threads may be inactive, thereby performing a no-operation (NOP) instead of executing the instruction. The SM 340 may be described in more detail below in conjunction with FIG. 4.

The MMU 390 provides an interface between the GPC 250 and the partition unit 280. The MMU 390 may provide translation of virtual addresses into physical addresses, memory protection, and arbitration of memory requests. In one embodiment, the MMU 390 provides one or more translation lookaside buffers (TLBs) for improving translation of virtual addresses into physical addresses in the memory 204.

Figure 3B:
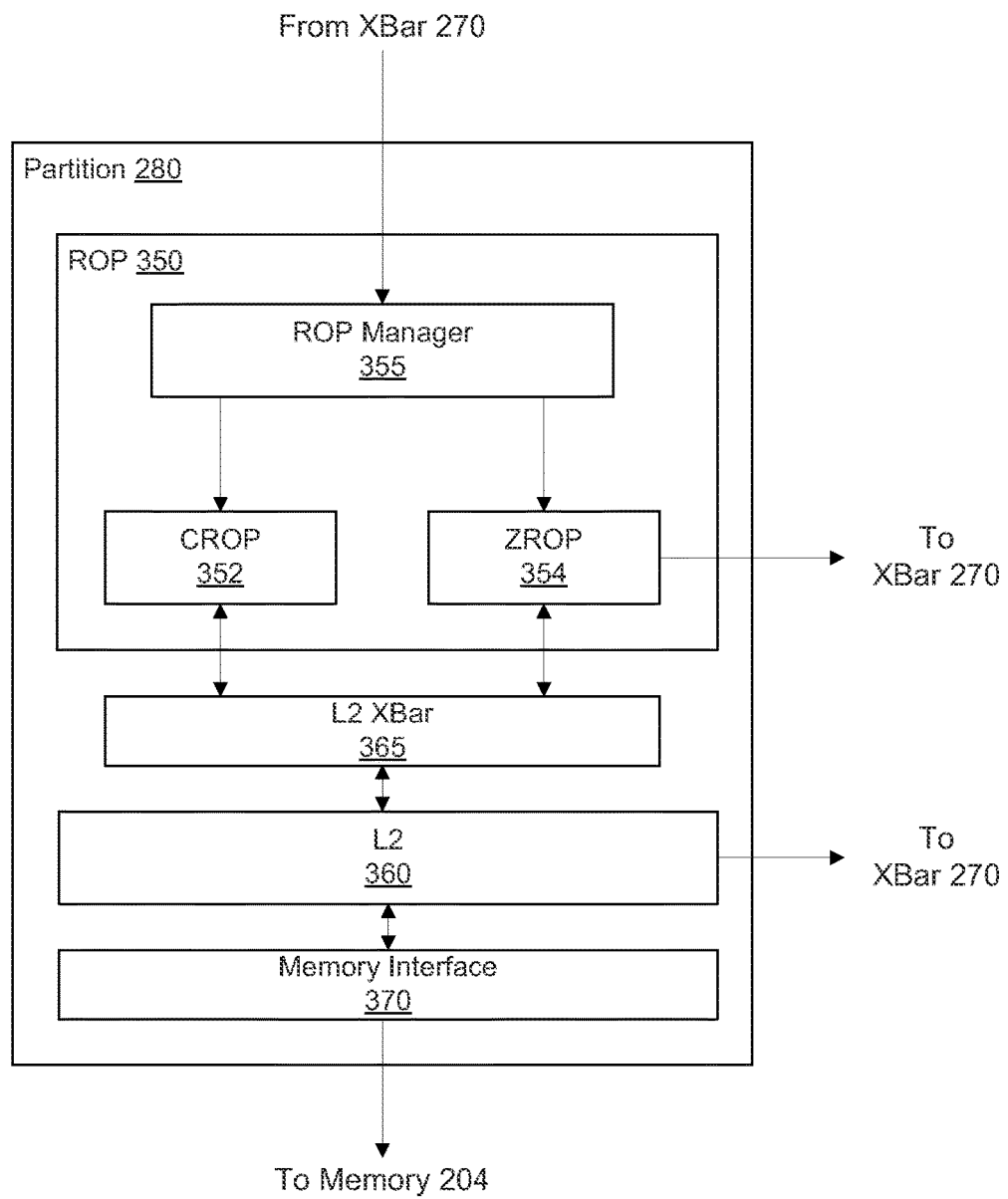
FIG. 3B illustrates a partition unit of the parallel processing unit of FIG. 2, in accordance with one embodiment.

FIG. 3B illustrates a partition unit 280 of the PPU 200 of FIG. 2, in accordance with one embodiment. As shown in FIG. 3B, the partition unit 280 includes a Raster Operations (ROP) unit 350, a level two (L2) cache 360, a memory interface 370, and an L2 crossbar (XBar) 365. The memory interface 370 is coupled to the memory 204. Memory interface 370 may implement 16, 32, 64, 128-bit data buses, or the like, for high-speed data transfer. In one embodiment, the PPU 200 comprises U memory interfaces 370, one memory interface 370 per partition unit 280, where each partition unit 280 is connected to a corresponding memory device 204. For example, PPU 200 may be connected to up to U memory devices 204, such as graphics double-data-rate, version 5, synchronous dynamic random access memory (GDDR5 SDRAM). In one embodiment, the memory interface 370 implements a DRAM interface and U is equal to 6.

In one embodiment, the PPU 200 implements a multi-level memory hierarchy. The memory 204 is located off-chip in SDRAM coupled to the PPU 200. Data from the memory 204 may be fetched and stored in the L2 cache 360, which is located on-chip and is shared between the various GPCs 250. As shown, each partition unit 280 includes a portion of the L2 cache 360 associated with a corresponding memory device 204. Lower level caches may then be implemented in various units within the GPCs 250. For example, each of the SMs 340 may implement a level one (L1) cache. The L1 cache is private memory that is dedicated to a particular SM 340. Data from the L2 cache 360 may be fetched and stored in each of the L1 caches for processing in the functional units of the SMs 340. The L2 cache 360 is coupled to the memory interface 370 and the XBar 270.

The ROP unit 350 includes a ROP Manager 355, a Color ROP (CROP) unit 352, and a Z ROP (ZROP) unit 354. The CROP unit 352 performs raster operations related to pixel color, such as color compression, pixel blending, and the like. The ZROP unit 354 implements depth testing in conjunction with the raster engine 325. The ZROP unit 354 receives a depth for a sample location associated with a pixel fragment from the culling engine of the raster engine 325. The ZROP unit 354 tests the depth against a corresponding depth in a depth buffer for a sample location associated with the fragment. If the fragment passes the depth test for the sample location, then the ZROP unit 354 updates the depth buffer and transmits a result of the depth test to the raster engine 325. The ROP Manager 355 controls the operation of the ROP unit 350. It will be appreciated that the number of partition units 280 may be different than the number of GPCs 250 and, therefore, each ROP unit 350 may be coupled to each of the GPCs 250. Therefore, the ROP Manager 355 tracks packets received from the different GPCs 250 and determines which GPC 250 that a result generated by the ROP unit 350 is routed to. The CROP unit 352 and the ZROP unit 354 are coupled to the L2 cache 360 via an L2 XBar 365.

Figure 4:
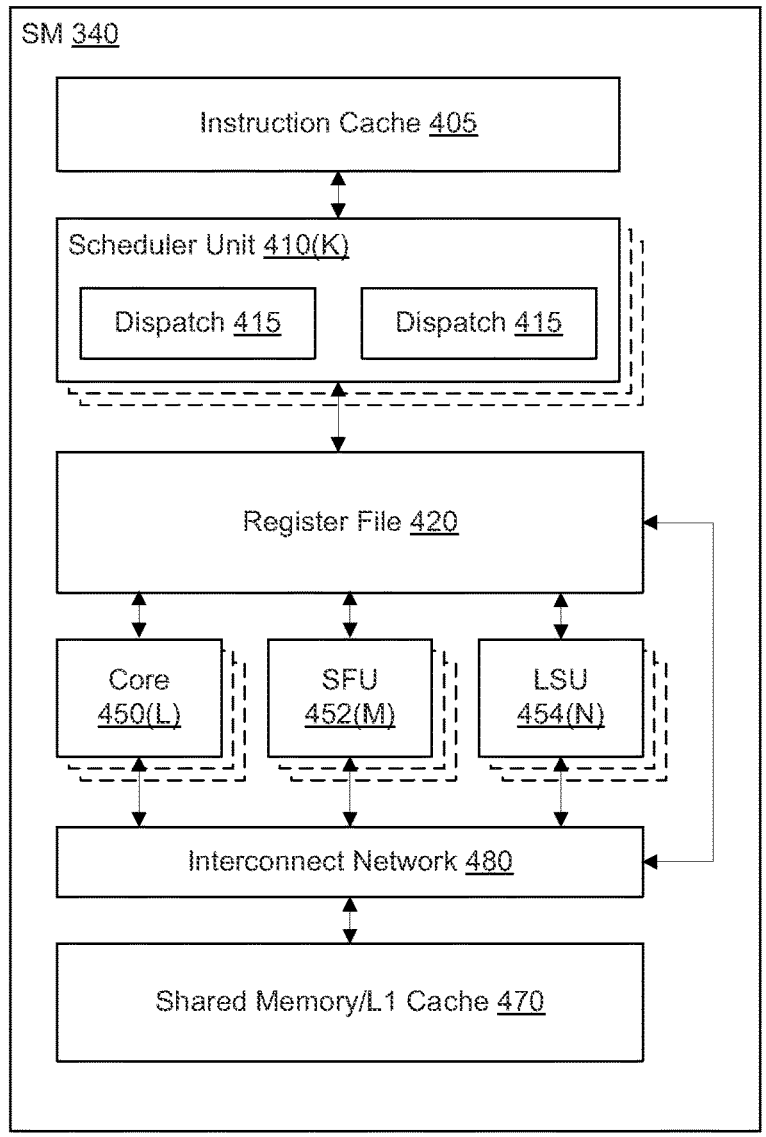
FIG. 4 illustrates the streaming multi-processor of FIG. 3A, in accordance with one embodiment.

FIG. 4 illustrates the streaming multi-processor 340 of FIG. 3A, in accordance with one embodiment. As shown in FIG. 4, the SM 340 includes an instruction cache 405, one or more scheduler units 410, a register file 420, one or more processing cores 450, one or more special function units (SFUs) 452, one or more load/store units (LSUs) 454, an interconnect network 480, and a shared memory/L1 cache 470.

As described above, the work distribution unit 225 dispatches tasks for execution on the GPCs 250 of the PPU 200. The tasks are allocated to a particular TPC 320 within a GPC 250 and, if the task is associated with a shader program, the task may be allocated to an SM 340. The scheduler unit 410 receives the tasks from the work distribution unit 225 and manages instruction scheduling for one or more groups of threads (i.e., warps) assigned to the SM 340. The scheduler unit 410 schedules threads for execution in groups of parallel threads, where each group is called a warp. In one embodiment, each warp includes 32 threads. The scheduler unit 410 may manage a plurality of different warps, scheduling the warps for execution and then dispatching instructions from the plurality of different warps to the various functional units (i.e., cores 350, SFUs 352, and LSUs 354) during each clock cycle.

In one embodiment, each scheduler unit 410 includes one or more instruction dispatch units 415. Each dispatch unit 415 is configured to transmit instructions to one or more of the functional units. In the embodiment shown in FIG. 4, the scheduler unit 410 includes two dispatch units 415 that enable two different instructions from the same warp to be dispatched during each clock cycle. In alternative embodiments, each scheduler unit 410 may include a single dispatch unit 415 or additional dispatch units 415.

Each SM 340 includes a register file 420 that provides a set of registers for the functional units of the SM 340. In one embodiment, the register file 420 is divided between each of the functional units such that each functional unit is allocated a dedicated portion of the register file 420. In another embodiment, the register file 420 is divided between the different warps being executed by the SM 340. The register file 420 provides temporary storage for operands connected to the data paths of the functional units.

Each SM 340 comprises L processing cores 450. In one embodiment, the SM 340 includes a large number (e.g., 192, etc.) of distinct processing cores 450. Each core 450 may include a fully-pipelined, single-precision processing unit that includes a floating point arithmetic logic unit and an integer arithmetic logic unit. The core 450 may also include a double-precision processing unit including a floating point arithmetic logic unit. In one embodiment, the floating point arithmetic logic units implement the IEEE 754-2008 standard for floating point arithmetic. Each SM 340 also comprises M SFUs 452 that perform special functions (e.g., pixel blending operations, and the like), and N LSUs 454 that implement load and store operations between the shared memory/L1 cache 470 and the register file 420. In one embodiment, the SM 340 includes 192 cores 450, 32 SFUs 452, and 32 LSUs 454.

Each SM 340 includes an interconnect network 480 that connects each of the functional units to the register file 420 and the shared memory/L1 cache 470. In one embodiment, the interconnect network 480 is a crossbar that can be configured to connect any of the functional units to any of the registers in the register file 420 or the memory locations in shared memory/L1 cache 470.

The shared memory/L1 cache 470 is an array of on-chip memory that, in one embodiment, may be configured as either shared memory or an L1 cache, or a combination of both, as the application demands. For example, the shared memory/L1 cache 470 may comprise 64 kB of storage capacity. The shared memory/L1 cache 470 may be configured as 64 kB of either shared memory or L1 cache, or a combination of the two such as 16 kB of L1 cache and 48 kB of shared memory.

The PPU 200 described above may be configured to perform highly parallel computations much faster than conventional CPUs. Parallel computing has advantages in graphics processing, data compression, biometrics, stream processing algorithms, and the like.

In one embodiment, the PPU 200 comprises a graphics processing unit (GPU). The PPU 200 is configured to receive commands that specify shader programs for processing graphics data. Graphics data may be defined as a set of primitives such as points, lines, triangles, quads, triangle strips, and the like. Typically, a primitive includes data that specifies a number of vertices for the primitive (e.g., in a model-space coordinate system as well as attributes associated with each vertex of the primitive. The PPU 200 can be configured to process the graphics primitives to generate a frame buffer (i.e., pixel data for each of the pixels of the display).

An application writes model data for a scene (i.e., a collection of vertices and attributes) to a memory such as a system memory or memory 204. The model data defines each of the objects that may be visible on a display. The application then makes an API call to the driver kernel that requests the model data to be rendered and displayed. The driver kernel reads the model data and writes commands to the one or more streams to perform operations to process the model data. The commands may reference different shader programs to be implemented on the SMs 340 of the PPU 200 including one or more of a vertex shader, hull shader, domain shader, geometry shader, and a pixel shader. For example, one or more of the SMs 340 may be configured to execute a vertex shader program that processes a number of vertices defined by the model data. In one embodiment, the different SMs 340 may be configured to execute different shader programs concurrently. For example, a first subset of SMs 340 may be configured to execute a vertex shader program while a second subset of SMs 340 may be configured to execute a pixel shader program. The first subset of SMs 340 processes vertex data to produce processed vertex data and writes the processed vertex data to the L2 cache 360 and/or the memory 204. After the processed vertex data is rasterized (i.e., transformed from three-dimensional data into two-dimensional data in screen space) to produce fragment data, the second subset of SMs 340 executes a pixel shader to produce processed fragment data, which is then blended with other processed fragment data and written to the frame buffer in memory 204. The vertex shader program and pixel shader program may execute concurrently, processing different data from the same scene in a pipelined fashion until all of the model data for the scene has been rendered to the frame buffer. Then, the contents of the frame buffer are transmitted to a display controller for display on a display device.

The PPU 200 may be included in a desktop computer, a laptop computer, a tablet computer, a smart-phone (e.g., a wireless, hand-held device), personal digital assistant (PDA), a digital camera, a hand-held electronic device, and the like. In one embodiment, the PPU 200 is embodied on a single semiconductor substrate. In another embodiment, the PPU 200 is included in a system-on-a-chip (SoC) along with one or more other logic units such as a reduced instruction set computer (RISC) CPU, a memory management unit (MMU), a digital-to-analog converter (DAC), and the like.

In one embodiment, the PPU 200 may be included on a graphics card that includes one or more memory devices 204 such as GDDR5 SDRAM. The graphics card may be configured to interface with a PCIe slot on a motherboard of a desktop computer that includes, e.g., a northbridge chipset and a southbridge chipset. In yet another embodiment, the PPU 200 may be an integrated graphics processing unit (iGPU) included in the chipset (i.e., Northbridge) of the motherboard.

Multi-Stage Translation of Virtual Addresses

Figure 5A:
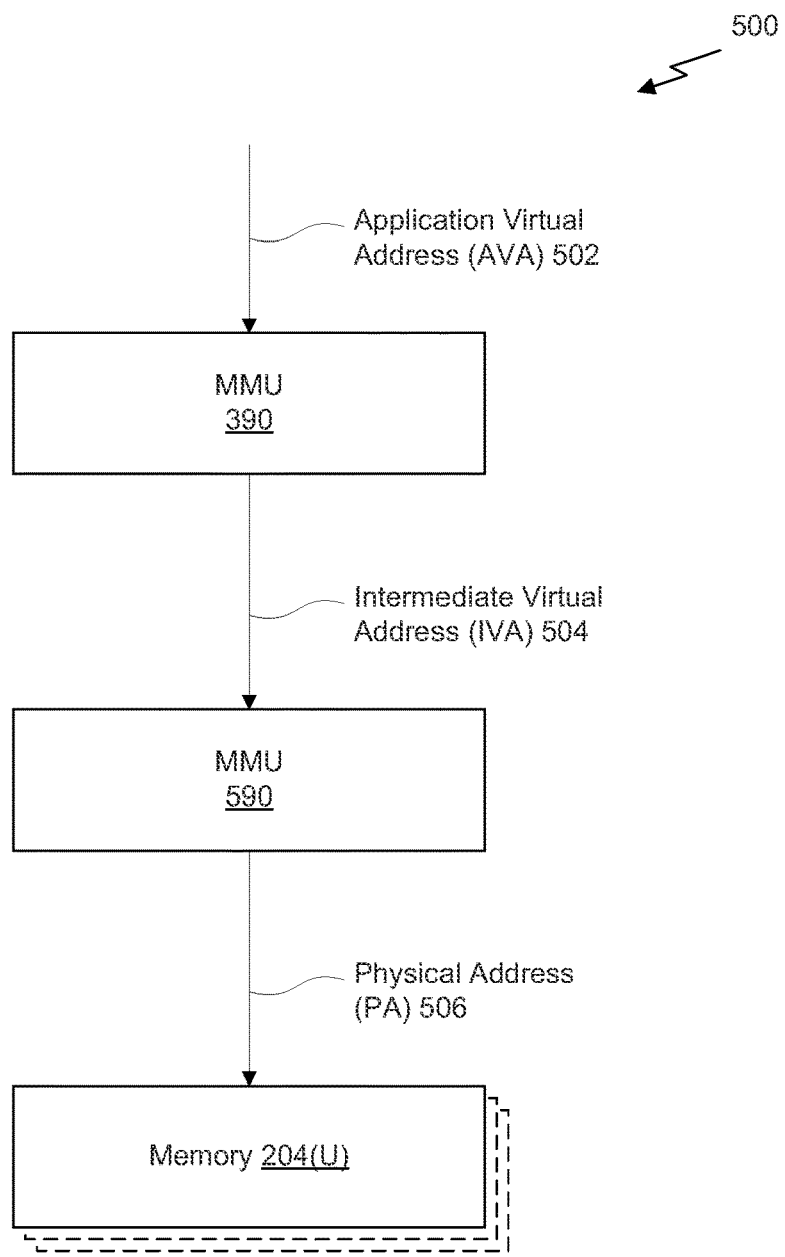
FIG. 5A illustrates multi-stage translation of virtual addresses, in accordance with one embodiment.

FIG. 5A illustrates multi-stage translation of virtual addresses, in accordance with one embodiment. As shown, a system 500 may include a plurality of MMUs. In one embodiment, the system 500 may be a system-on-chip (SoC) that includes the PPU (including the MMU 390), a host processor (i.e., central processing unit or CPU), and a system MMU. For example, the system 500 may include multiple MMUs such as at least one MMU 390 per GPC 250 of the PPU 200 and a system MMU 590 that is external to the PPU 200 and shared by multiple components on the SoC. In another embodiment, the PPU 200 may include a separate MMU in, e.g., each partition unit 280 that performs similar functions to the MMU 590 except that the MMU in each partition unit 280 would translate virtual addresses only for those physical addresses associated with a particular memory device 204.

As shown, a first MMU 390 receives an AVA 502. In one embodiment, the AVA 502 is a 40-bit address. In another embodiment, the AVA 502 is a 64-bit address. It will be appreciated that the AVA 502 may be any number of bits. The first MMU 390 performs a first translation that generates an IVA 504 from the AVA 502. The IVA 504 may then be transmitted to the second MMU 590. The IVA 504 may have a format that is similar to the AVA 502 (e.g., both the AVA 502 and the IVA 504 may have the same number of bits). The second MMU 590 performs a second translation that generates a PA 506 from the IVA 504. The PA 506 may have a format that is similar to the AVA 502 and the IVA 504. The PA 506 represents a memory location in a physical memory device such as a memory device 204. In one embodiment, the size of the AVA 502, the IVA 504, and the PA 506 may be varied depending on the address space associated with each of the aforementioned addresses. For example, the AVA 502 and IVA 504 may be 64-bits and the PA 506 may be 32-bits. Such an implementation would enable the virtual address space to be much larger than the physical address space implemented by the memory system.

In order to perform the first translation, the MMU 390 may utilize page tables configured for a particular page table size. For example, the MMU 390 may be configured to utilize one or more page tables corresponding to a page size of, e.g., 64 KB. In one embodiment, the MMU 390 implements a translation utilizing one page table. The page table divides the application address space into pages of a particular size. The MMU 390 utilizes a first portion of the AVA 502 as an index into the page table. The corresponding page table entry includes a base address for the IVA 504 that, when combined with a second portion of the AVA 502, is used to generate the IVA 504 in an intermediate address space. Each entry in the page table may include one or more attributes associated with the corresponding page of virtual memory in the application address space. In one embodiment, the one or more attributes may include compression information that defines a compression format for data stored in the page of virtual memory and addressing information for the compression state of the page. The attributes included in the page table entries for the first page table may be required to access information in the memory 204 because, for example, the information stored in that memory may only be decompressed using information in the attributes.

In another embodiment, the MMU 390 may implement a multi-level translation using a page table hierarchy of two or more page tables. In other words, a first level page table may divide the application address space into a plurality of regions, each region including a plurality of pages. For example, the first level page table may divide the application address space into, e.g., 16 MB regions. The MMU 390 may utilize a first portion of the AVA 502 to determine an index into the first level page table. The corresponding entry in the first level page table provides a base address for a second level page table corresponding to that particular region. The second level page table includes a plurality of page table entries corresponding to the plurality of pages for the region. A second portion of the AVA 502 is used to determine an index into the second level page table. The corresponding entry in the second level page table provides a base address for the IVA 504 that, when combined with a third portion of the AVA 502, is used to generate the IVA 504 in the intermediate address space. Although a multi-level page table hierarchy having two levels is described above, a multi-level page table hierarchy having more than two levels may be implemented.

A second translation is then performed by the MMU 590 that generates the PA 506 in a physical address space from the IVA 504 in the intermediate address space. The second translation may be performed similar to the first translation described above utilizing a different set of one or more page tables. For example, the MMU 590 may be configured to utilize one or more page tables corresponding to a page size of, e.g., 4 KB in the physical address space. Thus, the first translation performed by the MMU 390 maps addresses in the application address space to pages of virtual memory in the intermediate address space, such pages having a first size. The second translation performed by the MMU 590 maps addresses in the intermediate address space to pages of physical memory in the physical address space, such pages having a second size that may be the same as the first size or different from the first size. In one embodiment, the first size may be larger than the second size in order to reduce the size of page tables in the first set of page tables.

As described above, each of the MMUs may include one or more TLBs used to cache page table entries associated with the translation of the AVA 502 into the IVA 504 or the IVA 504 into the PA 506. During operation, the chance of a miss occurring in the TLB may be reduced by using larger page sizes. Even though an operating system may require the system MMU 590 to utilize small pages such as 4 KB, the MMU 390 may be configured to use pages of a larger size that increases the efficiency of the system. Furthermore, some attributes may be needed by systems that utilize the first MMU 390 and are logically separated from the second MMU 590 such that the attributes cannot be provided by the second MMU 590. If those attributes are not required by any systems logically below the first MMU 390 (i.e., systems that process instructions associated with the IVA 504 address space), then those attributes may not need to be stored in the page table entries associated with the second MMU 590. Such an implementation may reduce the size of the page tables in the memory.

Translating the AVA 502 into the IVA 504 and ultimately the PA 506 may result in a cache miss in the TLBs of the corresponding MMU. The TLB miss will trigger the MMU to retrieve the page from the memory 204. In one embodiment, the page table entry may be stored in the TLB (such that there is no cache miss), but the page table entry may be marked as invalid, protected (e.g., read-only), priv_protected (e.g., read/write access for only privileged clients), and so forth. Page table entries marked as such, when accessed by a memory request, will trigger a page fault error. The page fault error may be handled by software. In one embodiment, a page fault error generated by the first MMU 390 may be handled differently than when a page fault error is generated by the second MMU 590. In other words, software may handle page fault errors differently for different stages of translation.

Again, it will be noted that the AVA 502 may be associated with larger page sizes such that some algorithms that require larger contiguous regions to be efficient may be implemented on systems that require the IVA 504 to be associated with small page table sizes such as 4 KB. For example, caching of compression state information may be more efficient for larger page sizes where compression state is only changed between larger boundaries of contiguous memory such as every 64 KB or 1 MB.

In yet another embodiment, the multi-stage translation may include more than two stages. For example, a three-stage translation may be implemented using three MMUs. A first MMU translates the AVA 502 into a first IVA 504. A second MMU translates the first IVA 504 into a second IVA. Finally, a third MMU translates the second IVA into the PA 506. It will be appreciated that any number of intermediate stages may be implemented using additional MMUs.

In still yet another embodiment, the MMU 390 may be configurable. In other words, the MMU 390 may be configured to translate the AVA 502 to the IVA 504 or, alternatively, to translate the AVA 502 directly to the PA 506 in a single stage translation. In the case that the MMU 390 is configured to translate the AVA 502 directly to the PA 506, the MMU 390 may be configured to transmit a signal to any downstream MMUs such as the MMU 590 that disables the downstream MMU from performing a translation of the PA 506. Thus, the system can be configured for either single stage or multi-stage translation using the same hardware. In another embodiment, the MMU 390 does not transmit a signal to the MMU 590, but rather a host processor is programmed to configure the MMU 390 and the MMU 590 according to a mode of operation.

In some embodiments, the page table entries include a bit that indicates whether translation of an address in that particular page table should be single stage or multi-stage. For example, if the bit is logic low, then single stage translation is performed in the MMU 390 translates the AVA 502 directly to the PA 506 and the MMU 590 is disabled downstream. However, if the bit is logic high, then multi-stage translation is performed in the MMU 390 (translating the AVA 502 to the IVA 504) and the MMU 590 (translating the IVA 504 to the PA 506). It will be appreciated that different page table entries within the same page table may be configured with different modes of operation such that some addresses will be translated using single stage translation and other addresses will be translated using multi-stage translation.

Figure 5B:
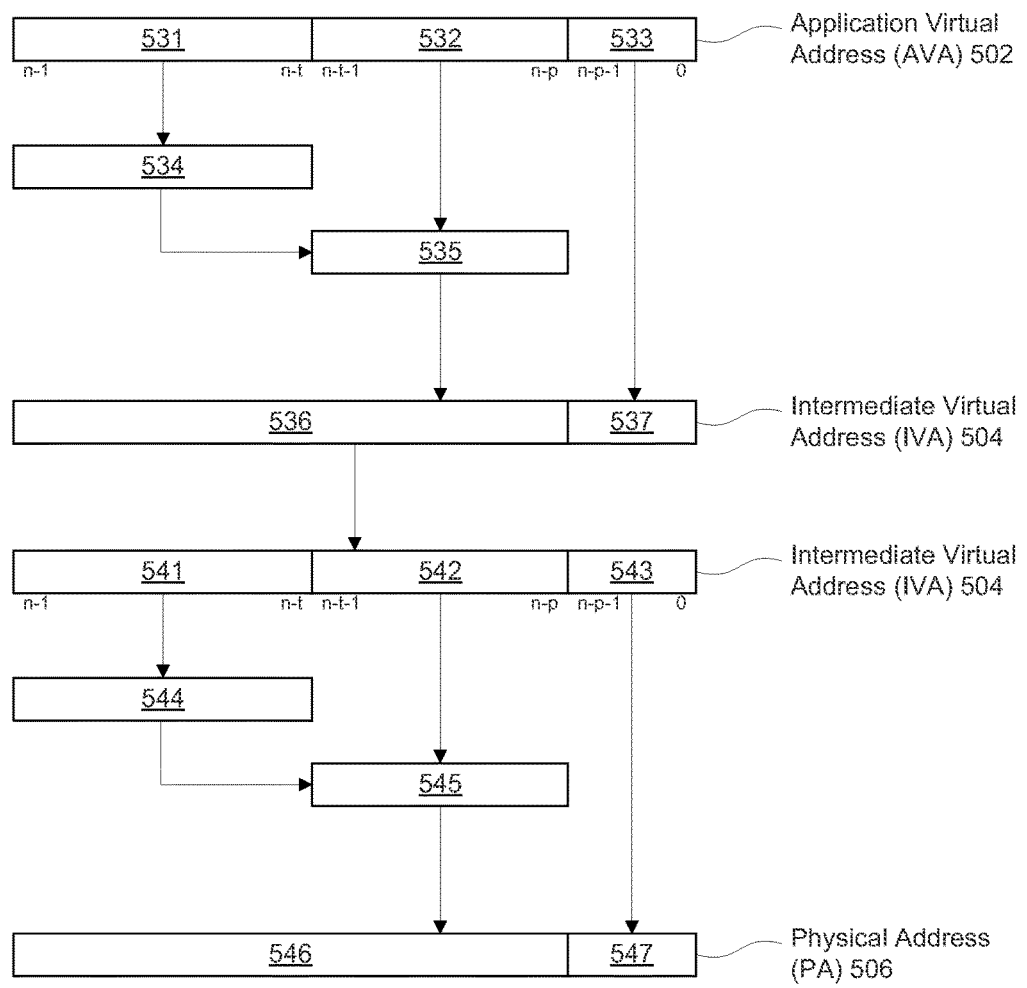
FIG. 5B illustrates translations of an application virtual address to an intermediate virtual address and the intermediate virtual address to a physical address, in accordance with one embodiment.

FIG. 5B illustrates translations of an AVA 502 to an IVA 504 and the IVA 504 to a PA 506, in accordance with one embodiment. As shown in FIG. 5B, the AVA 502 includes n bits. In one embodiment n is equal to 40. The AVA 502 may comprise a number of portions used for the translation. In one embodiment, a first portion 531 is used as an index into a first level page table. The first portion 531 includes the t most significant bits of the AVA 502. The size of t is based on the size of the regions associated with the first level page table. For example, with application address space memory regions of 64 KB size and 40-bit virtual addresses, t is equal to 24 and the first portion equals the 24 MSBs of the AVA 502. Based on the first portion 531, a page table entry 534 from the first level page table is selected and a base address of a second level page table is read from the page table entry 534. A second portion 532 of the AVA 502 is used as an index into the second level page table. The second portion 532 includes a next number of bits of the AVA 502. The size of the second portion is determined by subtracting the number t from a number p. The size of p is based on the size of the pages associated with the second level page table. For example, with pages of 4 KB size, p is equal to 28. If t is equal to 24, then the size of the second portion 532 is equal to 4 bits. Based on the second portion 532, a page table entry 535 from the second level page table is selected and a base address 536 of the IVA 504 is read from the page table entry 535. The base address 536 of the IVA 504 is combined with an offset 537 represented by the third portion 533 of the AVA 502. For example, the third portion 533 may be, e.g., the 12 least significant bits (LSBs) of the AVA 502.

As also shown in FIG. 5B, the IVA 504 is then translated in a similar fashion to generate the PA 506. In one embodiment, the IVA 504 also includes n bits. Alternatively, the IVA 504 may be a different number of bits than the AVA 502. Again, the IVA 504 may comprise a number of portions used for the translation. In one embodiment, a first portion 541 is used as an index into a first level page table. The first portion 541 includes the t most significant bits of the IVA 504. Based on the first portion 541, a page table entry 544 from the first level page table is selected and a base address of a second level page table is read from the page table entry 544. A second portion 542 of the IVA 504 is used as an index into the second level page table. Based on the second portion 542, a page table entry 545 from the second level page table is selected and a base address 546 of the PA 506 is read from the page table entry 545. The base address 546 of the PA 506 is combined with an offset 547 represented by the third portion 543 of the IVA 504. Again, the PA 506 may be n-bits or a different number of bits from either the AVA 502 or the IVA 504.

It will be appreciated that the sizes of the portions for the AVA 502 and the IVA 504 may not be the same. For example, the second MMU 590 may implement a translation using a single page table such that the IVA 504 comprises only a first portion that represents an index into the page table and a second portion that represents an offset of the PA 506. In alternative embodiments, the second MMU 590 may implement a multi-level page table hierarchy that utilizes different sized regions in the first level page table such that the size of the first portions and second portions are different in the AVA 502 and the IVA 504.

Figure 5C:
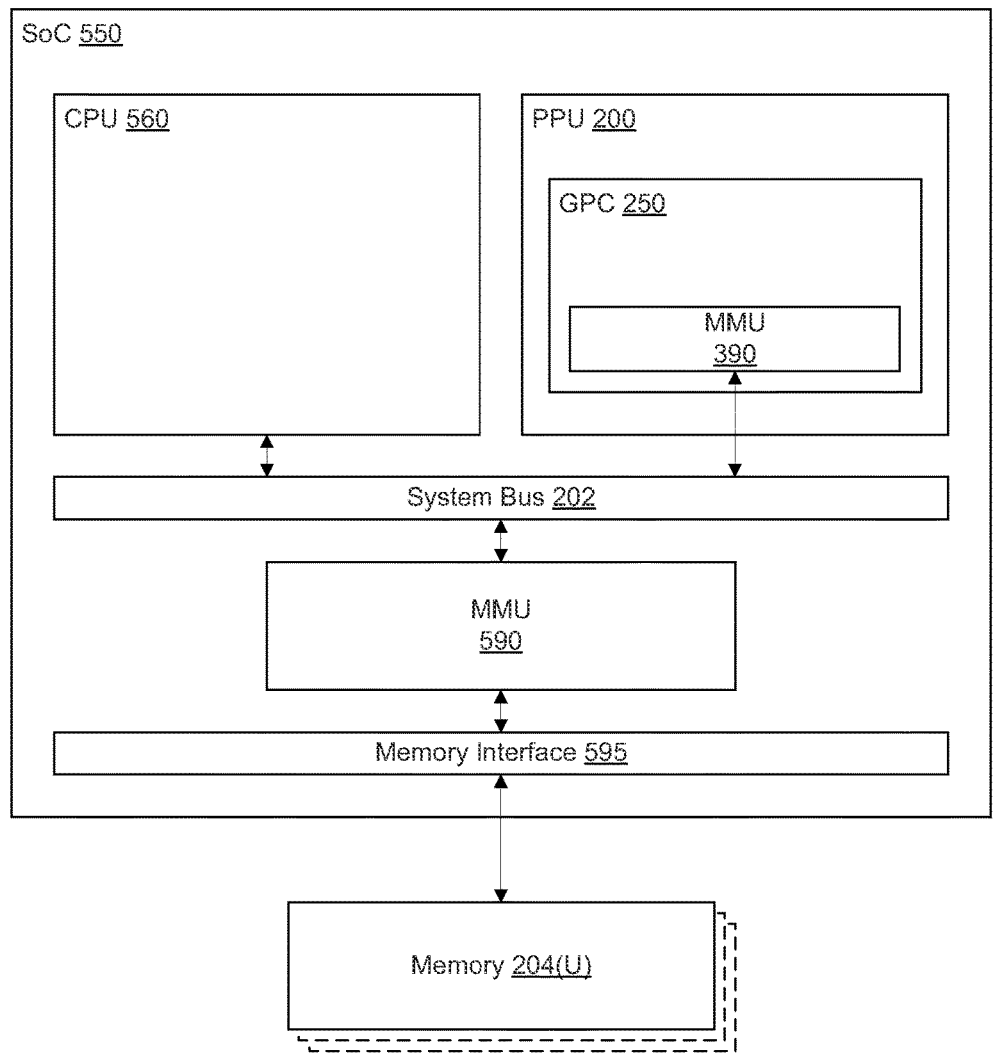
FIG. 5C illustrates a system configured to implement a multi-stage translation, in accordance with one embodiment.

FIG. 5C illustrates a system configured to implement a multi-stage translation, in accordance with one embodiment. As shown in FIG. 5C, the system may be a System-on-Chip (SoC) 550 that includes a CPU 560 and a PPU 200, as described above. The SoC 550 may also include a system bus 202 to enable communication between the various components of the SoC 550. Memory requests generated by the CPU 560 and the PPU 200 may be routed through the system MMU 590 that is shared by multiple components of the SoC 550. The SoC 550 may also include a memory interface 595 that is coupled to one or more memory devices 204 through, e.g., a DRAM interface.

As described above, program instructions executed by the GPC 250 may cause memory access requests to be generated and transmitted to the MMU 390. The memory access requests may include an AVA 502 in the application address space. The MMU 390 translates the AVA 502 into an IVA 504 and transmits a new memory access request that includes the IVA 504 to the MMU 590. The MMU 590 translates the IVA 504 into a PA 506 and transmits a new memory request that includes the PA 506 to the memory device 204 via the memory interface 595.

Figure 6A:
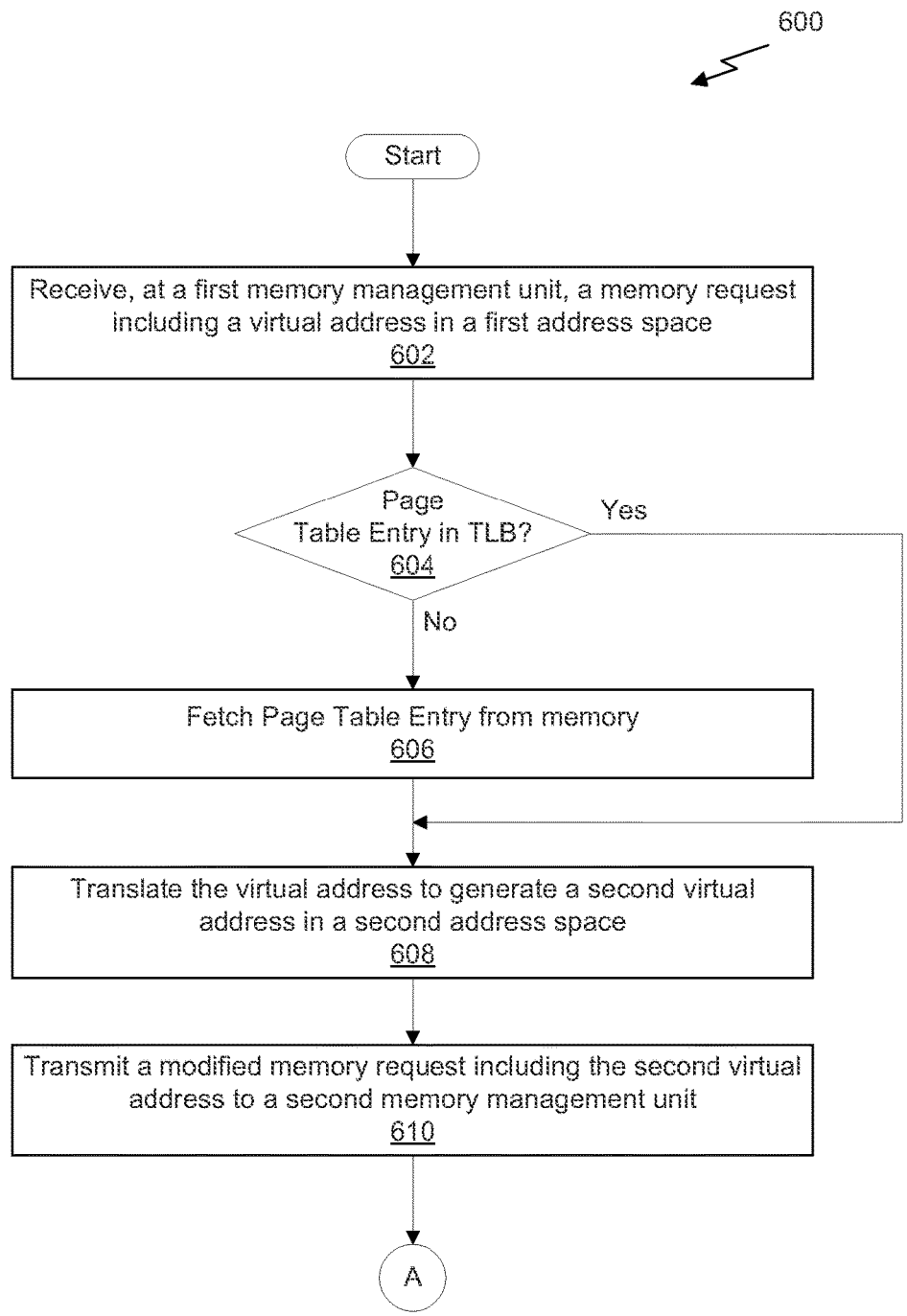
FIGS. 6A & 6B illustrate a flowchart of a method for multi-stage translation of a virtual address to a physical address, in accordance with another embodiment.
Figure 6B:
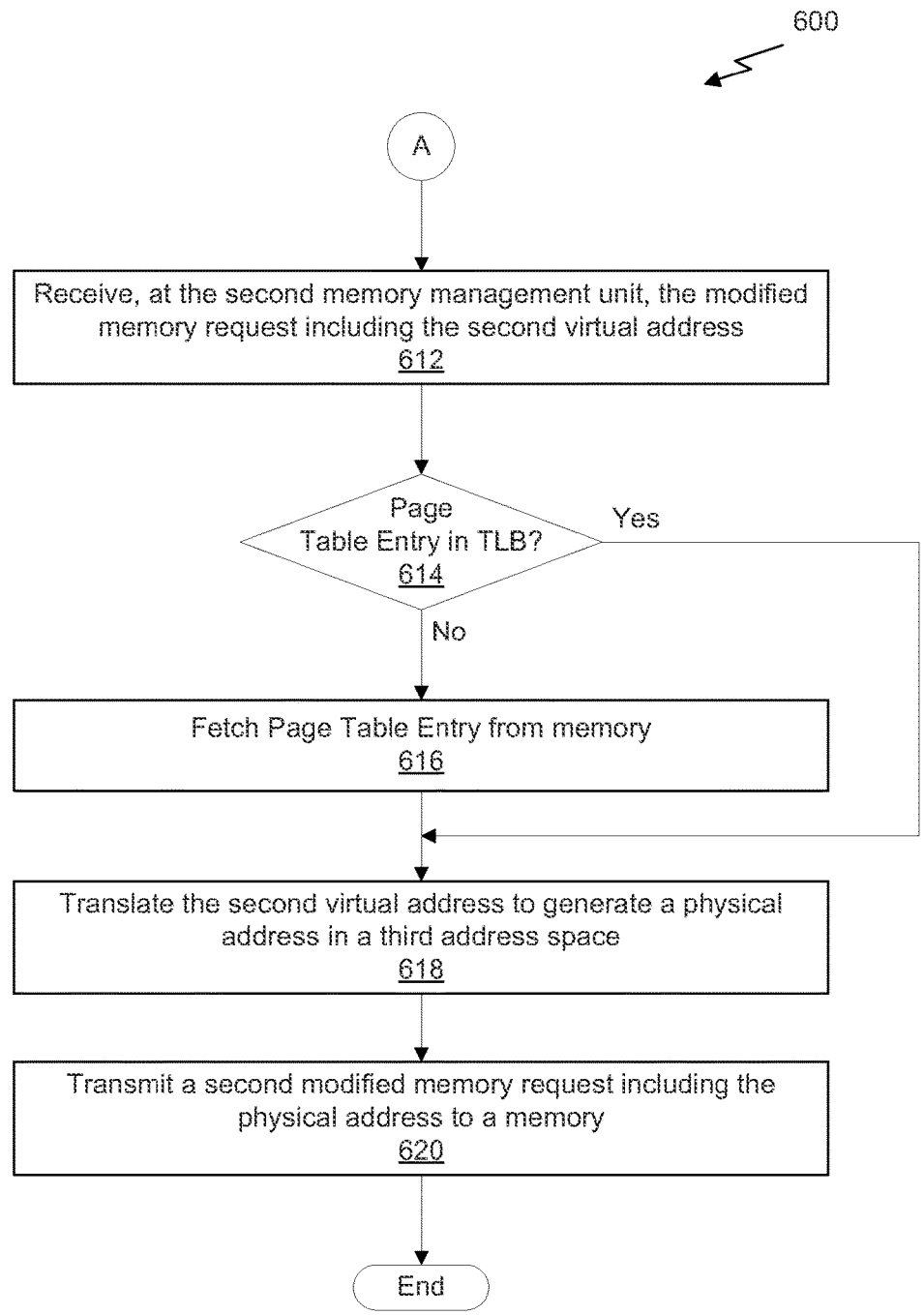

FIGS. 6A & 6B illustrate a flowchart of a method 600 for multi-stage translation of a virtual address to a physical address, in accordance with another embodiment. At step 602, a MMU 390 receives a memory request including a virtual address in a first address space. At step 604, the MMU 390 determines whether a copy of a page table entry associated with the virtual address is stored in a TLB of the MMU 390. If the TLB does not store a copy of the page table entry associated with the virtual address, then, at step 606, the MMU 390 fetches the copy of the page table entry from the memory. In one embodiment, in order to fetch the copy of the page table entry from the memory, the MMU 390 generates a memory request to read the page table entry associated with the virtual address from the memory. After transmitting the memory request to the memory, the MMU 390 receives a response for the memory request that includes data representing a copy of the page table entry. The MMU 390 stores the data representing a copy of the page table entry associated with the virtual address in a slot of the TLB. After the page table entry is stored in the TLB, the method 600 proceeds to step 608.

Returning to step 604, if the TLB includes a copy of the page table entry associated with the virtual address, then, at step 608, the MMU 390 translates the virtual address to generate a second virtual address in a second address space. The translation is performed based, at least in part, on information included in the page table entry stored in the TLB. At step 610, the MMU 390 transmits a modified memory request including the second virtual address to a MMU 590.

At step 612, the MMU 590 receives the modified memory request including the second virtual address from the MMU 390. At step 614, the MMU 590 determines whether a copy of a page table entry associated with the second virtual address is stored in a TLB of the MMU 590. If the TLB does not store a copy of the page table entry associated with the second virtual address, then, at step 616, the MMU 590 fetches the copy of the page table entry from the memory. The page table entry associated with the second virtual address may be different from the page table entry associated with the virtual address. In other words, the page table entries, even though they relate to the same physical page, may include different information such as different addresses for performing a translation and different attributes associated with the corresponding page of memory.

Returning to step 614, if the TLB includes a copy of the page table entry associated with the second virtual address, then, at step 618, the MMU 590 translates the second virtual address to generate a physical address in a third address space. The translation is performed based, at least in part, on information included in the page table entry stored in the TLB. At step 620, the MMU 590 transmits a second modified memory request including the physical address to the memory.

Figure 7:
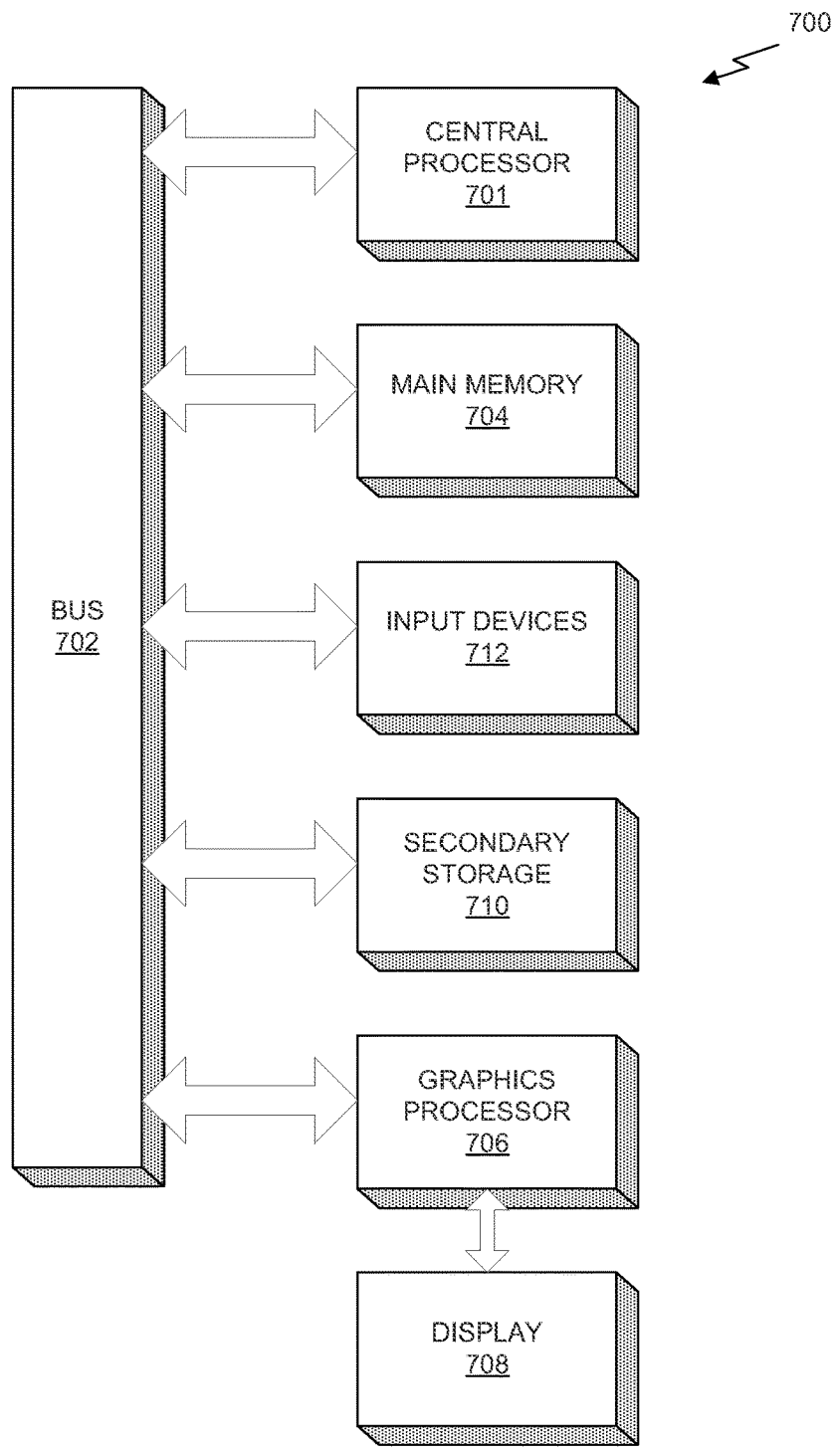
FIG. 7 illustrates an exemplary system in which the various architecture and/or functionality of the various previous embodiments may be implemented.

FIG. 7 illustrates an exemplary system 700 in which the various architecture and/or functionality of the various previous embodiments may be implemented. As shown, a system 700 is provided including at least one central processor 701 that is connected to a communication bus 702. The communication bus 702 may be implemented using any suitable protocol, such as PCI (Peripheral Component Interconnect), PCI-Express, AGP (Accelerated Graphics Port), HyperTransport, or any other bus or point-to-point communication protocol(s). The system 700 also includes a main memory 704. Control logic (software) and data are stored in the main memory 704 which may take the form of random access memory (RAM).

The system 700 also includes input devices 712, a graphics processor 706, and a display 708, i.e. a conventional CRT (cathode ray tube), LCD (liquid crystal display), LED (light emitting diode), plasma display or the like. User input may be received from the input devices 712, e.g., keyboard, mouse, touchpad, microphone, and the like. In one embodiment, the graphics processor 706 may include a plurality of shader modules, a rasterization module, etc. Each of the foregoing modules may even be situated on a single semiconductor platform to form a graphics processing unit (GPU).

In the present description, a single semiconductor platform may refer to a sole unitary semiconductor-based integrated circuit or chip. It should be noted that the term single semiconductor platform may also refer to multi-chip modules with increased connectivity which simulate on-chip operation, and make substantial improvements over utilizing a conventional central processing unit (CPU) and bus implementation. Of course, the various modules may also be situated separately or in various combinations of semiconductor platforms per the desires of the user.

The system 700 may also include a secondary storage 710. The secondary storage 710 includes, for example, a hard disk drive and/or a removable storage drive, representing a floppy disk drive, a magnetic tape drive, a compact disk drive, digital versatile disk (DVD) drive, recording device, universal serial bus (USB) flash memory. The removable storage drive reads from and/or writes to a removable storage unit in a well-known manner.

Computer programs, or computer control logic algorithms, may be stored in the main memory 704 and/or the secondary storage 710. Such computer programs, when executed, enable the system 700 to perform various functions. The memory 704, the storage 710, and/or any other storage are possible examples of computer-readable media.

In one embodiment, the architecture and/or functionality of the various previous figures may be implemented in the context of the central processor 701, the graphics processor 706, an integrated circuit (not shown) that is capable of at least a portion of the capabilities of both the central processor 701 and the graphics processor 706, a chipset (i.e., a group of integrated circuits designed to work and sold as a unit for performing related functions, etc.), and/or any other integrated circuit for that matter.

Still yet, the architecture and/or functionality of the various previous figures may be implemented in the context of a general computer system, a circuit board system, a game console system dedicated for entertainment purposes, an application-specific system, and/or any other desired system. For example, the system 700 may take the form of a desktop computer, laptop computer, server, workstation, game consoles, embedded system, and/or any other type of logic. Still yet, the system 700 may take the form of various other devices including, but not limited to a personal digital assistant (PDA) device, a mobile phone device, a television, etc.

Further, while not shown, the system 700 may be coupled to a network (e.g., a telecommunications network, local area network (LAN), wireless network, wide area network (WAN) such as the Internet, peer-to-peer network, cable network, or the like) for communication purposes.

While various embodiments have been described above, it should be understood that they have been presented by way of example only, and not limitation. Thus, the breadth and scope of a preferred embodiment should not be limited by any of the above-described exemplary embodiments, but should be defined only in accordance with the following claims and their equivalents.

What is claimed is:

1. A method comprising:
   receiving, at a first memory management unit, a memory request including a virtual address in a first address space;
   translating the virtual address to generate a second virtual address in a second address space using a first page table including entries configured for a first page size, wherein the first page table entries include a first attribute that is consistent for pages of the first page size including a first physical page in a memory; and
   transmitting a modified memory request including the second virtual address to a second memory management unit,
   wherein the second memory management unit is configured to translate the second virtual address to generate a physical address in a third address space using a second page table including entries configured for a second page size that is different compared with the first page size, wherein the second page table entries include a second attribute that is consistent for pages of the second page size and varies for pages of the first page size including the first physical page,
   wherein the physical address is associated with a location in the first physical page, and
   wherein the first memory management unit and the second memory management unit are implemented in hardware.

2. The method of claim 1, wherein the first address space comprises an application address space.

3. The method of claim 1, wherein the first memory management unit includes a translation lookaside buffer (TLB).

4. The method of claim 3, further comprising:
   determining that the TLB does not include a copy of a page table entry associated with the virtual address;
   generating a memory request to read the page table entry associated with the virtual address from the memory;
   receiving a response for the memory request including data representing the copy of the page table entry associated with the virtual address; and
   storing the data representing the copy of the page table entry associated with the virtual address in a slot of the TLB.

5. The method of claim 4, wherein the data representing the copy of the page table entry associated with the virtual address includes the first attribute that is associated with a page of memory corresponding to the page table entry associated with the virtual address.

6. The method of claim 5, wherein the second memory management unit includes a second TLB, and wherein the second memory management unit, in response to receiving the modified memory request, is further configured to:
   determine that the second TLB does not include a copy of a page table entry associated with the second virtual address;
   generate a second memory request to read the page table entry associated with the second virtual address from the memory;
   receive a response for the memory request including data representing the copy of the page table entry associated with the second virtual address; and
   store the data representing the copy of the page table entry associated with the second virtual address in a slot of the second TLB.

7. The method of claim 1, wherein the first attribute comprises a compression format for data stored in a first page of memory.

8. The method of claim 1, wherein the first attribute comprises an address that points to compression state information for a first page of memory.

9. The method of claim 1, wherein the entries in the first page table each include a bit indicating whether the first memory management unit is configured to translate the virtual address in the first address space directly to the physical address in the third address space and the second memory management unit is disabled for the virtual address.

10. The method of claim 1, wherein the memory request including the virtual address in the first address space is generated by a third memory management unit in response to receiving a memory request including a third virtual address in a third address space.

11. The method of claim 10, wherein the third address space comprises an application address space, the first address space comprises a first intermediate address space, and the second address space comprises a second intermediate address space.

12. The method of claim 1, wherein the first page size is larger than the second page size and the first attribute is associated with the first page size and is not associated with the second page size.

13. The method of claim 1, wherein a size of the virtual address and a size of the physical address are not equal.

14. The method of claim 1, wherein the first attribute is not stored in the second page table and the second attribute is not stored in the first page table.

15. A system comprising: a first memory management unit configured to:
receive a memory request including a virtual address in a first address space,
translate the virtual address to generate a second virtual address in a second address space using a first page table including entries configured for a first page size, wherein the first page table entries include a first attribute that is consistent for pages of the first page size including a first physical page in a memory, and
transmit a modified memory request including the second virtual address to a second memory management unit;
and the second memory management unit configured to:
translate the second virtual address to generate a physical address in a third address space using a second page table including entries configured for a second page size that is different compared with the first page size, wherein the second page table entries include and a second attribute that is consistent for pages of the second page size and varies for pages of the first page size including the first physical page,
wherein the physical address is associated with a location in the first physical page,
wherein the first memory management unit and the second memory management unit are implemented in hardware.

16. The system of claim 15, wherein the first memory management unit includes a translation lookaside buffer (TLB), the first memory management unit further configured to:
determine that the TLB does not include a copy of a page table entry associated with the virtual address;
generate a memory request to read the page table entry associated with the virtual address from the memory;
receive a response for the memory request including data representing the copy of the page table entry associated with the virtual address; and
store the data representing the copy of the page table entry associated with the virtual address in a slot of the TLB.

17. The system of claim 15, wherein the first memory management unit is included in a parallel processing unit.

18. The system of claim 17, wherein the parallel processing unit is included in a system-on-chip (SoC) that includes a central processing unit and the second memory management unit coupled to a system bus.

19. The system of claim 15, wherein the first page size is larger than the second page size and the first attribute is associated with the first page size and is not associated with the second page size.

20. The system of claim 15, wherein the first attribute is not stored in the second page table and the second attribute is not stored in the first page table.

* * * * *

UNITED STATES PATENT AND TRADEMARK OFFICE
CERTIFICATE OF CORRECTION

PATENT NO. : 10,114,760 B2
APPLICATION NO. : 14/155278
DATED : October 30, 2018
INVENTOR(S) : Steven E. Molnar et al.

It is certified that error appears in the above-identified patent and that said Letters Patent is hereby corrected as shown below:

In the Specification

Column 2, Line 1 please replace "unit, if accordance" with --unit, in accordance--;
Column 3, Line 58 please replace "205 Implements" with --205 implements--;
Column 9, Line 5 please replace "coordinate system as" with --coordinate system) as--.

Signed and Sealed this
Seventeenth Day of March, 2020

Andrei Iancu
*Director of the United States Patent and Trademark Office*